United States Patent [19]

Ampel

[11] Patent Number: 5,556,150
[45] Date of Patent: Sep. 17, 1996

[54] MULTIPURPOSE PROBE

[75] Inventor: Stuart Ampel, Boca Raton, Fla.

[73] Assignee: Ampel Probe Corporation, Boca Raton, Fla.

[21] Appl. No.: 323,231

[22] Filed: Oct. 14, 1994

Related U.S. Application Data

[63] Continuation-in-part of Ser. No. 267,473, Jun. 28, 1994, abandoned.

[51] Int. Cl.$^6$ ............................................. B25B 7/02
[52] U.S. Cl. ............................................. 294/118; 294/902
[58] Field of Search ............................... 294/8.5, 11, 16, 294/28, 99.2, 104, 106, 118, 1.1, 902; 273/84 R; 81/487, 488

[56] References Cited

U.S. PATENT DOCUMENTS

| | | | |
|---|---|---|---|
| 1,093,400 | 4/1914 | Gottfrid | 294/11 B |
| 1,857,979 | 5/1932 | Schaefer | 294/11 B |
| 2,239,108 | 4/1941 | Lindemann | 294/11 B |
| 2,559,978 | 7/1951 | Marco | 294/118 X |
| 2,668,538 | 2/1954 | Baker | 294/118 X |
| 2,977,150 | 3/1961 | Thomas | 294/118 |
| 3,153,554 | 10/1964 | Beihl | 294/118 X |
| 3,552,792 | 1/1971 | Granat et al. | 294/118 X |
| 3,906,957 | 9/1975 | Weston | 294/99.2 |
| 4,023,450 | 5/1977 | Ygfors | 81/418 |
| 4,483,221 | 11/1984 | Hoskins | 294/118 X |
| 4,620,386 | 11/1986 | Hare | 294/118 X |
| 5,161,842 | 11/1992 | Beeler | 294/1.1 |
| 5,203,241 | 4/1993 | Mattis | 81/424 |

*Primary Examiner*—Dean Kramer
*Attorney, Agent, or Firm*—Howrey & Simon; Stephen J. Rosenman; C. Scott Talbot

[57] ABSTRACT

A probe for detecting and handling objects that are hidden from sight or from which it is desirable to insulate the user from direct contact includes pivotally coupled elements with jaw and handle portions. The jaw portions are preferably angled with respect to the handle portions to facilitate insertions into pockets of search subjects' clothing, and the elements are preferably formed of composite materials with high vibration transmissivity.

15 Claims, 3 Drawing Sheets

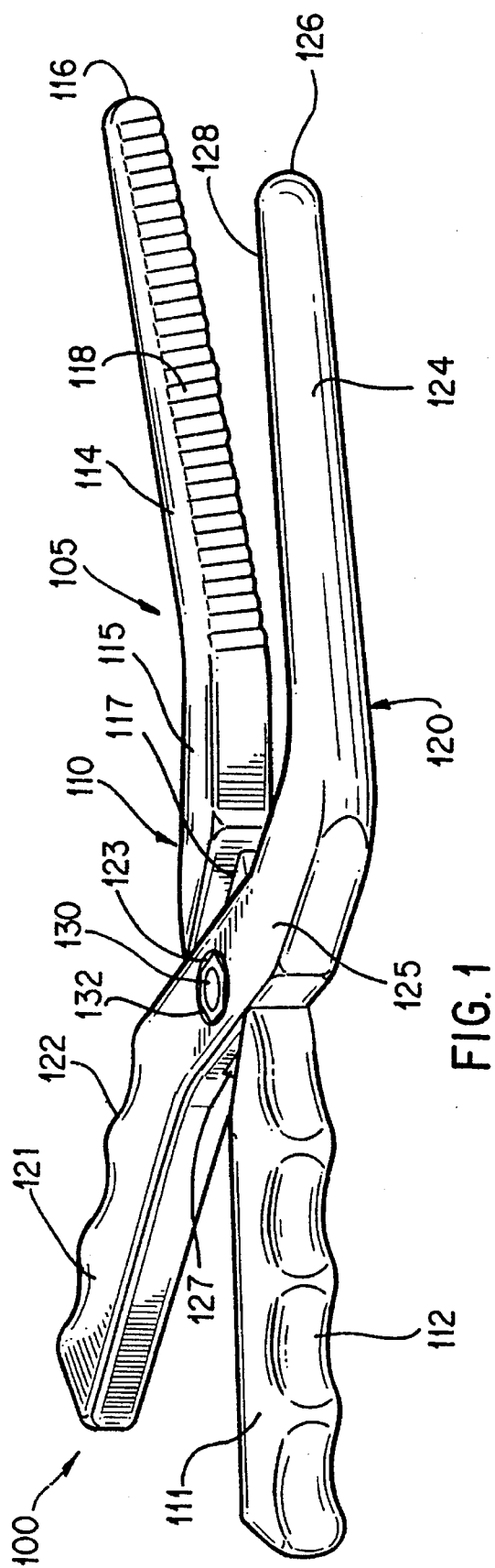
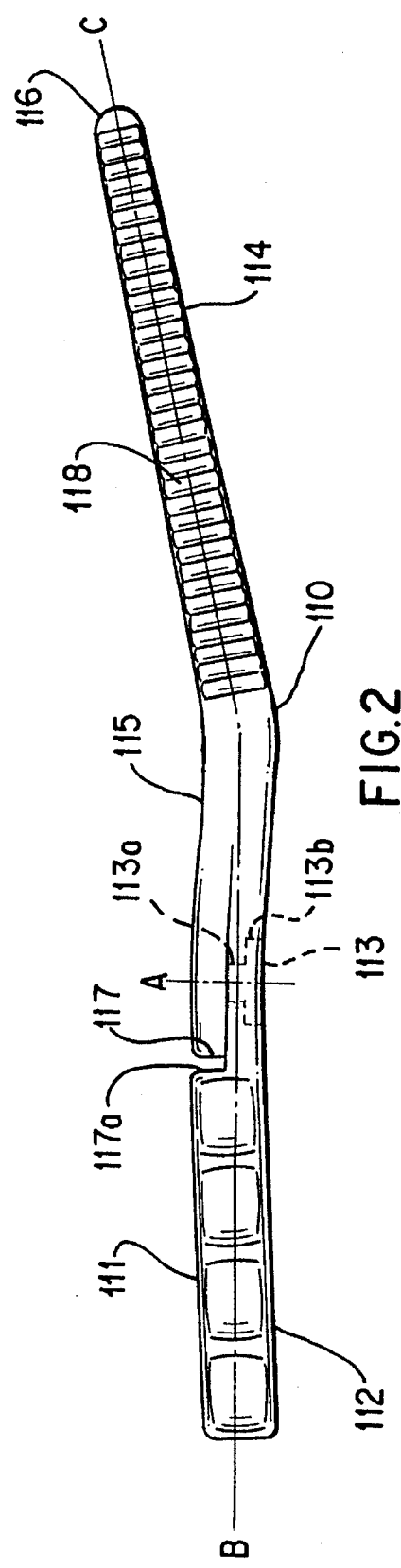
FIG.1
FIG.2

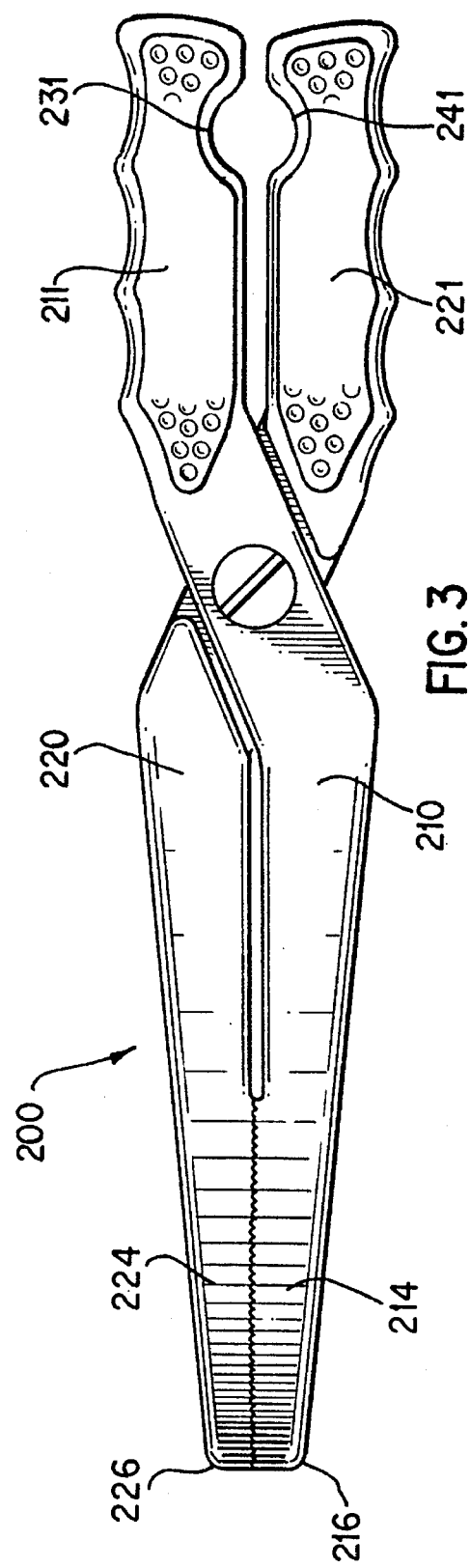
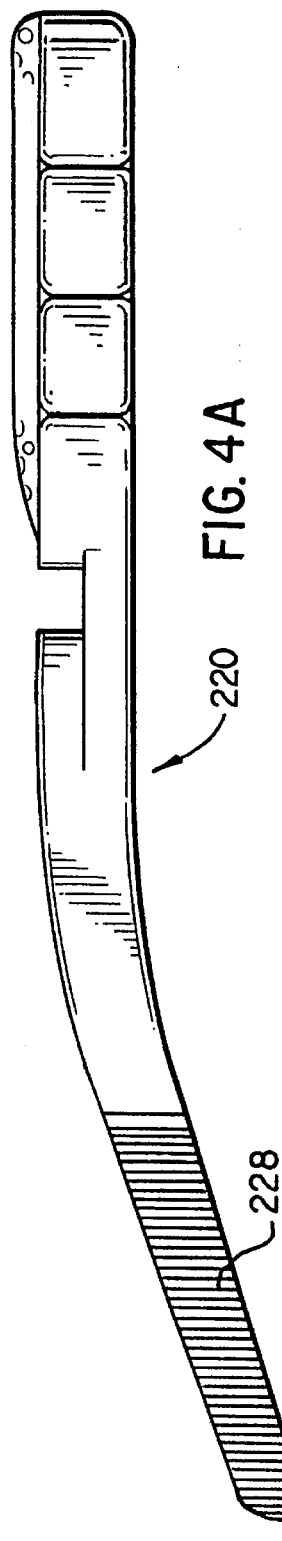
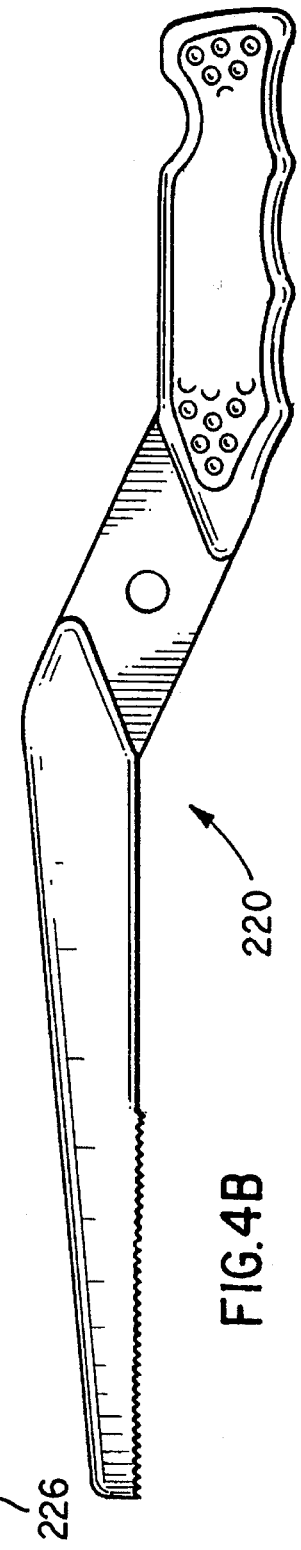
FIG. 3
FIG. 4A
FIG. 4B

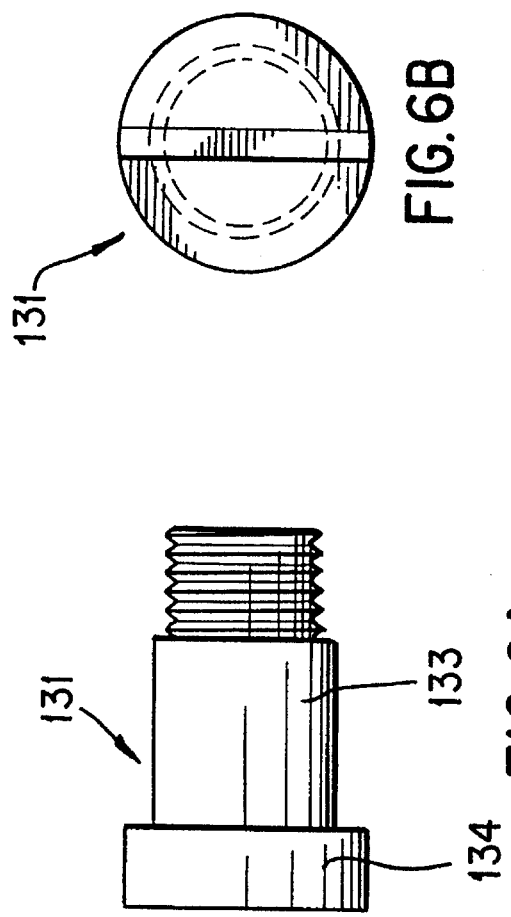
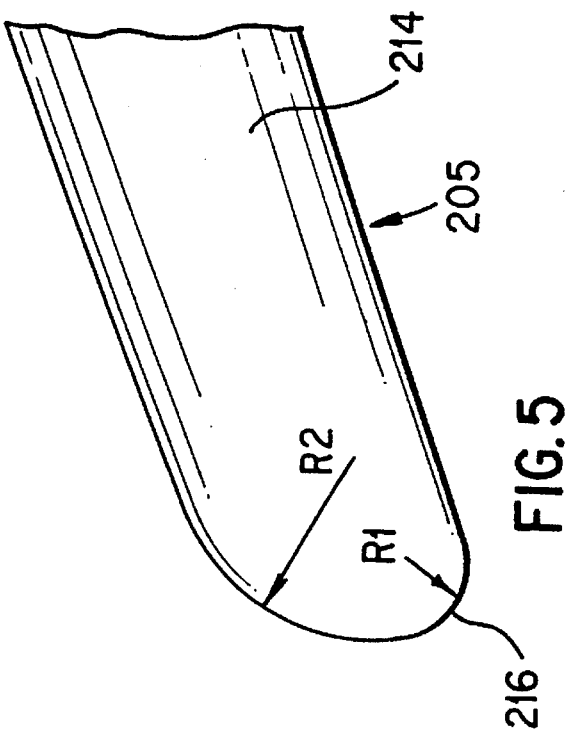

MULTIPURPOSE PROBE

BACKGROUND OF THE INVENTION

This application is a continuation-in-part of U.S. patent application Ser. No. 08/267,473, filed Jun. 28, 1994, now abandoned.

This invention relates generally to probes and pliers for handling objects, and more particularly to a probe for detecting and handling objects that are hidden from sight or from which it is desirable to insulate the user from direct contact.

There are many situations in which it is desirable to detect or handle an object that is hidden or from which it is desirable to insulate the user from direct contact. For example, in the field of law enforcement, peace officers frequently need to search suspects' persons or belongings to locate and remove weapons, contraband material, or evidence. Conventionally, the peace officer conducts such searches by hand. This presents several risks and problems. First, with increasing frequency peace officers encounter hidden objects such as hypodermic needles and waste materials that may conduct on contact such infectious diseases as AIDS and hepatitis. Other hazards that may be encountered include discharge of firearms or explosion of ammunition or explosives, and shock from electrical devices. Second, inadvertent manual contact with evidence may damage or otherwise alter or contaminate the evidence (such as by obliterating fingerprints). Third, a peace officer manually searching the person of a suspect of the opposite sex is subject to allegations of improperly touching the suspect, and in many situations it is impractical to await the arrival of a peace officer of the same sex as the suspect.

All of these risks are amplified when the peace officer searches the suspect's trouser pockets. The front trouser pockets are one of the most productive areas to search (because these pockets are so frequently used by suspects to carry objects of potential interest to the searcher) but are also difficult and hazardous to search by hand because the front pockets are typically deep, relatively tight, and difficult to access because the pocket often wraps over the front of the wearer's hip. The peace officer may be able to detect an object from the outside of the pocket, but often has difficulty extracting the object because the peace officer's hand must be held relatively flat to reach over the suspects hip into the pocket, inhibiting the hand's dexterity. The rear pockets of trousers present similar difficulties. Although usually shallower than front pockets, rear pockets are usually tighter, and are usually disposed over the suspect's buttocks so that it is awkward for the peace officer to reach into the pocket. The peace officer is also more vulnerable to attack by the suspect when one of the peace officer's hands is essentially immobilized in the suspect's pocket.

The risks of infection or other hazard and damage to or contamination of objects are still present when the object is not hidden, such as when a peace officer or other investigator (such as an arson investigator, customs officer, insurance investigator, forensic specialist, security guard, etc.) sifts through material in the open. Similar risks are present to medical practitioners such as medical examiners, paramedics, and emergency room personnel.

There is therefore a need for a device that permits a user to detect or handle an object that is hidden or from which it is desirable to insulate the user from direct contact. There is a particular need for such a device to facilitate detection and removal of objects from the pockets of trousers being worn by a suspect. These needs have not been met by any available product.

SUMMARY OF THE INVENTION

This need is met by the probe of the present invention. The probe includes pivotally coupled elements with jaw and handle portions. The jaw portions are preferably angled with respect to the handle portions to facilitate insertion into pockets of search subjects' clothing, and are sufficiently long to reach to the bottoms of the pockets. The elements are preferably formed of a composite material with high strength, low density, high vibration transmissivity, resistant to high temperature and corrosive environments, electrically insulating, and subject to use in molding processes.

BRIEF DESCRIPTION OF THE DRAWINGS

FIG. 1 is a perspective view of a first embodiment of a probe embodying the principles of the invention.

FIG. 2 is a side elevation view of one element of the probe of FIG. 1.

FIG. 3 is a plan view of a second embodiment of a probe embodying the principles of the invention.

FIGS. 4A and B are plan and side elevation views of one element of the probe of FIG. 3.

FIG. 5 is a detail side elevation view of the tip end of the element of FIG. 4.

FIGS. 6A and B are side elevation and top plan views of a connecting bolt used to connect the elements of the probes of FIGS. 1 and 3.

DETAILED DESCRIPTION

Reference will now be made in detail to presently preferred embodiments of the invention, examples of which are illustrated in the accompanying drawings.

A first embodiment of a probe embodying the principles of the invention is illustrated in FIGS. 1 and 2. Probe 100 includes two essentially symmetrical probe elements 110, 120, pivotally coupled through central, coupling portions 115, 125 at a pivot axis A by a connector 130. Each probe element 110, 120 includes a handle portion 111, 121, and a jaw portion 114, 124, respectively. The handle portions 111, 121 (and the coupling portions 115, 125) lie substantially in a handle plane B, while the jaw portions 114, 124 lie substantially in a jaw plane C. Jaw plane C is disposed at an angle with respect to handle plane B, so that the overall shape of the probe is generally arcuate, with the upper side 105 of the probe (the side visible in FIG. 1) being generally concave.

Handle portions 111, 121 include finger grip portions 112, 122, respectively, formed on the laterally outer (with respect to pivot axis A) faces thereof, with arcuate recesses sized for comfortable gripping by a user's hand.

Jaw portions 114, 124 include textured portions 118, 128, which in this embodiment include a series of parallel grooves formed in a generally planar surface. Jaw portions 114, 124 also include tip ends 116, 126, which are symmetrically tapered with a relatively large, constant radius.

Coupling portions 115, 125 include a stepped connecting bore 113, 123 through which connector 130 is fitted to couple the elements 110, 120. Connector 130 includes a threaded pin 131 (shown in FIGS. 6A and 6B) and a matingly threaded nut 132 (best seen in FIG. 1). The shaft 133 of pin 131 fits through the smaller diameter portion 113a, of bore 113 and a corresponding smaller diameter portion (not shown) of bore 123, while the head 134 of pin 131 fits into larger diameter portion 113b of bore 113, and nut 132 fits into larger diameter portion of bore 123. The torque with which the nut and pin are threaded together determines the frictional resistance of the probe elements to relative pivoting in opening and closing the jaw portions. Mating recesses 117, 127 in coupling portions 115, 125 limit the extent to which elements 110, 120 can be pivoted (and thus to which jaw portions 114, 124 can be separated) by the engagement between shoulder 117a and a corresponding shoulder (not shown) in recess 127 and the adjacent side of the other coupling portion. At the other end of the range of pivotal motion of the elements, at least the tip ends 116, 126 are in contact.

A second, and presently preferred, embodiment of a probe embodying the principles of the present invention is illustrated in FIGS. 3 to 5. Probe 200 has essentially the same components and features as probe 100 (and each element is numbered correspondingly except that the initial digit is 2 rather than 1). The significant differences are identified below.

Handle portions 211, 221 include inner finger recesses 231, 241, respectively, on their laterally inner surfaces. The user can insert a finger between the finger recesses to aid in separating the handle portions during use.

Tip ends 216, 226 of jaw portions 214, 224, are asymmetrically tapered. As shown in FIG. 5 for tip end 216, the tip end is tapered with a relatively small radius R1 on the concave, upper side 205 of the probe, and with a relatively larger radius R2 on the opposite side. This asymmetrical taper allows the user to grasp relatively smaller objects and to fit the tip end into a smaller area to be searched than with the symmetrically tapered, larger radius tip end of the probe 100.

Jaw portions 214, 224 include textured portions (shown as 228 on jaw portion 224 in FIG. 4A, the corresponding textured portion of jaw portion 214 not being shown), which in this embodiment are formed with a series of parallel ridges with a triangular cross-section.

The dimensions of the probe are selected to enable a user to readily search areas such as trouser pockets. Accordingly, the probe is preferably approximately 12" (30 cm) in overall length, with the pivot axis A being closer to the handle end of the probe than the jaw end, so that jaw portions are 6" (15 cm) or longer. The elements are preferably pivotable through a range of motion of approximately 30°, and the tip ends can therefore be separated by up to approximately 4" (10 cm). Jaw plane C is preferably angled toward handle plane B by approximately 30°.

The probe elements are preferably made from a material that is strong, stiff, low density, and transmits vibrations well. High vibration transmissivity is particularly significant because it allows a user to detect a solid object that is hidden from view—if the jaw portions of the probe strike such an object, the vibrations will be efficiently transmitted to the handle portions where they can be sensed by the user. The material is also preferably resistant to corrosive and high temperature environments, and is electrically non-conductive. These properties permit handling objects that are hot, corrosive, or present shock hazards, and also permit heat or chemical sterilization of the probe after handling infectious materials or to avoid contaminating evidence. Thus, materials typically used in pliers and hemostats and similar surgical instruments (such as carbon steel, stainless steel, or aluminum) are not particularly suitable. Instead, composite materials are preferred, especially those with a polymer matrix and a strong and highly vibration transmissive fiber, such as glass.

In a particularly preferred embodiment, the probe elements are formed of chemically coupled, 50% long-glass fiber reinforced, heat stabilized polypropylene, sold under the trade name "VERTON" by LNP Engineering Plastics Inc. of Exton, Pa. and available as stock number MPX-700-10 HS. This material has a specific gravity of 1.34, a resin melt point of 325° F. (163° C.), a tensile strength of 18,500 psi (128 MPa), a flexural strength of 30,000 psi (207 MPa), and a flexural modulus of 1,500,000 psi (10,344 MPa). The material is suitable for use in injection molding processes, which allows flexible and low cost manufacture of the probe elements. It also offers the advantages that it can be molded in different colors to differentiate probes for usage by military, law enforcement, medical, etc. personnel, and is readily engraveable for personal identification.

The connector may be made of any suitable, high strength material, and in the preferred embodiment the connector pin and nut are formed of stainless steel.

In both embodiments, the angled or arcuate configuration facilitates insertion of the jaw portions of the probe into trouser pockets. The jaw portions can be inserted into a front trouser pocket of a search subject from behind the subject, with the concave, upper side of the probe against the user's hip so that the jaw portions are inserted over and around the front of the user's hip. Conversely, the jaw portions can be inserted into a rear trouser pocket with the upper side of the probe away from the user's buttock, which gives the user a less awkward grip on the handle portions. The probe can also be used to locate objects from outside the pocket by tapping the tip end against the pocket. If the tip ends strike a solid object through the fabric of the trouser, the resulting vibrations will be transmitted to the user's hand via the handle portions. The user can the insert the probe into the pocket and remove the object.

The probe can also be used in other situations in which it is desired to detect and remove a hazardous object hidden from view. One such situation is removing a fish hook embedded in the mouth of a fish.

Although not shown in the illustrated embodiments, it may be preferred in some circumstances for the handle portions to be formed as loops (like scissors handles). The loops permit somewhat easier opening of the jaw portions, and can protect the backs of the user's fingers. However, such loops present a hazard in any situation (such as typically encountered by peace officers) in which a confrontation may develop with the search subject—if the search subject seizes the probe while the peace officer is holding handle portions with closed loops, the officer's hand can be injured.

It may also be preferred that the probe elements be straight, rather than arcuate, if the probe will not be used in situations in which the arcuate shape is particularly useful (such as searching pockets), since a straight shape is somewhat easier to manufacture.

What is claimed is:

1. A probe for use by a user in detecting and removing objects from a hidden location, including the interior of a front trouser pocket of a human subject of a search by the use, said probe comprising: first and second probe elements, each of said probe elements having a handle portion, a nonarticulated jaw portion, and an intermediate coupling portion;

means for coupling said probe elements at said coupling portions for relative pivotal movement between a closed position in which said jaw portions are adjacent and an open position in which said jaw portions are separated, said probe elements enabling the user to reach to the bottom of a front trousers pocket while said handle portions are substantially outside the pocket.

2. The probe of claim 1, wherein said jaw portions lie generally in first, jaw plane, and said handle portions lie generally in a second, handle plane, said jaw plane being disposed at an angle with respect to said handle plane.

3. The probe of claim 2, wherein each of said jaw portions includes a tip end that is asymmetrically tapered in the direction in which said jaw plane is angled toward said handle plane.

4. The probe of claim 1, wherein said probe is formed of a material that readily transmits vibrations from said jaw portions to said handle portions, vibrations generated by contact between said jaw portions and a solid object being efficiently transmitted to said handle portions.

5. A probe for use by a user in manually detecting and removing substantially solid objects from locations hidden from the sight of the user, including the interior of a front trouser pocket of a human subject of a search by the user, said probe comprising:

first and second probe elements, each of said probe elements having a handle portion and a one piece jaw portion, said probe elements being formed of a material having a high vibration transmissivity to efficiently conduct vibrations from said jaw portions to said handle portions; and means for coupling said probe elements for relative movement between a closed position in which said jaw portions are adjacent and an open position in which said jaw portions are separated, whereby the user can detect a substantially solid object at the bottom of a front trousers pocket while said handle portions are substantially outside the pocket by sensing at said handle portions vibrations created by contact of said jaw portions with the object and transmitted through said jaw portions and handle portions.

6. The probe of claim 5, wherein said material is a composite material having a matrix material and a fiber material.

7. The probe of claim 6, wherein said matrix material is a polymer material.

8. The probe of claim 7, wherein said matrix material is a polypropylene.

9. The probe of claim 6, wherein said fiber material is glass.

10. The probe of claim 5, wherein said material has a low density.

11. A method for searching a hidden location on the person of a suspect for an object and removing the object, comprising the steps of: inserting into the hidden location a probe having first and second probe elements, each of said probe elements having a handle portion and a jaw portion;

detecting the object by contact with said jaw portions;

grasping the object between said jaw portions; and removing the object from the hidden location.

12. The method of claim 11 wherein: said probe is formed of a material that readily transmits vibrations from said jaw portions to said handle portions, vibrations generated by contact between said jaw portions and a solid object being efficiently transmitted to said handle portion; and said detecting step includes sensing at one of said handle portions vibrations generated by contact between a respective one of said jaw portions and the object.

13. The method of claim 11, wherein:

said hidden location is a front pocket of trousers worn by a suspect;

said jaw portions are oriented generally in a first, jaw plane, and said handle portions are oriented generally in a second, handle plane, said jaw plane being disposed at an angle with respect to said handle plane;

said inserting step includes orienting said probe so that said jaw plane is angled toward the suspect's body to facilitate insertion into the pocket.

14. A probe for use by a user in detecting and removing objects from a front pocket of trousers worn by a human subject of a search by the user, comprising:

first and second probe elements, each of said probe elements having a handle portion and a jaw portion, said jaw portion having a tip end distal from said handle portion, said probe elements being generally arcuate in elevation, having a degree of curvature sufficient to permit ready insertion of said elements into the front trouser pocket around the subject's hip, having an overall length adequate for said tip ends to reach the lower end of the trouser pocket while the handle portion is substantially outside the pocket; and means for coupling said probe elements for relative movement between a closed position in which said jaw portions are adjacent and an open position in which said jaw portions are separated, whereby said jaw portions are readily insertable into the trouser pocket to remove the object from the pocket.

15. The probe of claim 14, wherein said probe is formed of a material that readily transmits vibrations from said tip ends to said handle portions, vibrations generated by contact between said jaw portions and a solid object being efficiently transmitted to said handle portions.

* * * * *